United States Patent
Hoganson

(10) Patent No.: US 9,814,563 B1
(45) Date of Patent: Nov. 14, 2017

(54) HEMODYNAMICALLY OPTIMIZED SHUNT

(71) Applicant: David M. Hoganson, Brookline, MA (US)

(72) Inventor: David M. Hoganson, Brookline, MA (US)

(*) Notice: Subject to any disclaimer, the term of this patent is extended or adjusted under 35 U.S.C. 154(b) by 0 days.

(21) Appl. No.: 14/696,380

(22) Filed: Apr. 25, 2015

Related U.S. Application Data

(60) Provisional application No. 61/984,728, filed on Apr. 25, 2014.

(51) Int. Cl.
*A61F 2/07* (2013.01)
*A61F 2/06* (2013.01)
*A61M 27/00* (2006.01)
*A61B 17/11* (2006.01)

(52) U.S. Cl.
CPC ............... *A61F 2/06* (2013.01); *A61F 2/07* (2013.01); *A61M 27/002* (2013.01); *A61B 2017/1135* (2013.01); *A61F 2002/065* (2013.01); *A61F 2002/068* (2013.01)

(58) Field of Classification Search
CPC ............... A61F 2/06; A61F 2/08; A61F 2/07
USPC ................................ 623/1.35–1.48; 604/8
See application file for complete search history.

(56) References Cited

U.S. PATENT DOCUMENTS

| | | | | |
|---|---|---|---|---|
| 3,894,530 A * | 7/1975 | Dardik | ............ | A61L 27/3625 600/36 |
| 3,974,526 A * | 8/1976 | Dardik | ............ | A61F 2/06 600/36 |
| 4,487,567 A * | 12/1984 | Possis | ............ | A61F 2/062 249/186 |
| 4,909,979 A * | 3/1990 | Possis | ............ | A61F 2/062 264/230 |
| 5,443,497 A * | 8/1995 | Venbrux | ............ | A61F 2/06 604/8 |
| 5,492,826 A * | 2/1996 | Townsend | ............ | C12M 21/08 435/289.1 |
| 5,776,182 A * | 7/1998 | Bruchman | ............ | A61L 27/507 600/36 |
| 5,800,540 A * | 9/1998 | Chin | ............ | A61F 2/07 128/898 |
| 6,019,788 A * | 2/2000 | Butters | ............ | A61B 17/064 604/8 |
| 6,221,101 B1 * | 4/2001 | Harris | ............ | A61F 2/06 623/1.1 |

(Continued)

*Primary Examiner* — Suzette J Gherbi
(74) *Attorney, Agent, or Firm* — Ramberg IP, LLC

(57) ABSTRACT

The imperfect hemodymamics and non-endothelialized surface of the BT shunt and RV-PA conduit can be improved by utilizing a shape that has more uniform flow and lower shear stress. Accordingly, the shunt will have an acute takeoff angle with a fluted inlet portion that eliminates fluid separation and maintains the shear stress within or near the physiologic range. The distal aspect of the shunt may be fluted in one or both directions along the pulmonary artery to improve the flow transition and reduce the shear forces on the posterior wall the pulmonary artery. An autologous umbilical vein may be used as the shunt with fluted proximal and distal portions with an autologous endothelialized surface to minimize platelet deposition and thrombus formation. The umbilical vein shunt may have an external support for diameter constraint and maintaining the hemodynamically optimized fluted design.

6 Claims, 9 Drawing Sheets

(56) References Cited

U.S. PATENT DOCUMENTS

| | | | | |
|---|---|---|---|---|
| 6,280,467 B1 * | 8/2001 | Leonhardt | A61F 2/07 623/1.16 |
| 6,338,724 B1 * | 1/2002 | Dossa | A61F 2/064 604/6.16 |
| 6,371,981 B1 * | 4/2002 | Yang | A61B 17/11 623/1.13 |
| 6,554,856 B1 * | 4/2003 | Doorly | A61F 2/82 623/1.15 |
| 6,589,278 B1 * | 7/2003 | Harris | A61F 2/064 623/1.3 |
| 8,123,797 B2 * | 2/2012 | Anwar | A61B 17/11 623/1.36 |
| 8,808,362 B2 * | 8/2014 | Anwar | A61B 17/11 623/1.36 |
| 2002/0099394 A1 * | 7/2002 | Houser | A61B 17/11 606/153 |
| 2002/0183857 A1 * | 12/2002 | Yang | A61F 2/06 623/23.72 |
| 2003/0033008 A1 * | 2/2003 | Schmitt | A61F 2/06 623/1.51 |
| 2004/0215125 A1 * | 10/2004 | Brown | A61F 2/07 604/6.16 |
| 2006/0229710 A1 * | 10/2006 | O'Brien | A61F 2/06 623/1.35 |
| 2008/0294245 A1 * | 11/2008 | Lundh | A61F 2/06 623/1.35 |
| 2010/0121247 A1 * | 5/2010 | Yang | A61M 1/3655 604/8 |
| 2010/0204783 A1 * | 8/2010 | Nugent | A61F 2/06 623/1.41 |
| 2012/0191170 A1 * | 7/2012 | Cohen | A61F 2/06 623/1.3 |
| 2013/0102950 A1 * | 4/2013 | Difiore | A61B 17/11 604/8 |
| 2013/0110029 A1 * | 5/2013 | Dakin | A61B 17/11 604/8 |

* cited by examiner

HEMODYNAMICALLY OPTIMIZED SHUNT

CROSS-REFERENCE TO RELATED APPLICATION(S)

This patent document claims the benefit of U.S. Provisional Patent Application Ser. No. 61/984,728, filed on Apr. 25, 2014 in the name of David M. Hoganson. The entire contents of this commonly owned patent application are herein expressly incorporated by reference.

STATEMENT REGARDING FEDERALLY SPONSORED RESEARCH

None.

BACKGROUND OF THE INVENTION

Field of the Invention

The present invention relates to improvements in vascular grafts that are placed between a systemic artery and a pulmonary artery of the heart. Such vascular grafts are termed "shunts".

Complex congenital heart disease often requires surgical repair in the neonatal period, and shunts are centrally important for these operations. These shunts are grafts that are placed between a systemic artery and a pulmonary artery or the heart and pulmonary artery. Unfortunately, there are no endothelialized conduits available for these reconstructions, and PTFE vascular grafts are currently used. The current shape of the PTFE grafts for this use results in areas of non-physiologic flow in the grafts leading to risk of stenosis and thrombosis. The complication rate for PTFE shunt conduits is high and the impact is dramatic. The interstage mortality rate for patients after a modified Blalock Taussig (BT) shunt is 5-19% with shunt thrombosis thought to be a leading cause of the mortality. The right ventricle to pulmonary artery (RV-PA) shunt in the Stage I reconstruction for hypoplastic left heart syndrome can have over a 50% reintervention rate.

Implantation of a modified Blalock-Taussig (BT) shunt is a very important procedure for treating patients with complex congenital heart disease as it provides a source of controlled blood flow to the lungs. However, it remains a high risk procedure with a discharge mortality risk of 4 to 7.2% and a morbidity rate of 13.1%. In its current form, the BT shunt has three important limitations. Unlike the rest of the circulation where the resistance is in the small diameter arterioles, the shunt must act as a resistor to limit pulmonary blood flow based on its diameter and length. In achieving this, the shunt has higher blood flow velocities and thus higher shear stress than the rest of the circulation. Additionally, the shunt material currently used is a polytetrafluoroethylene (PTFE) plastic tube. The non-endothlialized PTFE surface is a nidus for platelet adhesion and buildup of fibrinous deposits that can lead to stenosis. Finally, the placement of the BT between the innominate (or R subclavian) artery and right pulmonary artery in its current design leads to imperfect hemodynamics within the shunt. Areas of flow separation and abnormally high and low shear stress in the shunt lead to platelet activation, buildup of platelet and fibrinous deposits with eventually stenosis or thrombosis in some patients. Clinically, the development of stenosis in BT shunts is significant as at the time of shunt takedown, 64% of BT shunts have greater than 25% narrowing and 21% have greater than 50% narrowing. The right ventricle to pulmonary artery (RV-PA) shunt used in many operations including the Norwood procedure for hypoplastic heart syndrome also has imperfect hemodynamics and currently uses the PTFE material with similar limitations of stenosis commonly requiring interventions.

These complications would likely be minimized with a shunt design with improved hemodynamics including lower shear stress and shear variation.

Although hemodynamic improvement of PTFE shunts would be a clinically important advance, there is opportunity for further improvement by providing an endothelialized shunt. A functioning endothelial surface would eliminate the foreign body contact with platelets in an area that already has physiologically aberrant flow.

As neonates have no suitable sized autologous arterial or venous conduit for shunt creation, the infants' own umbilical vein may serve as a conduit for the shunt. The diameter of the umbilical vein makes it an acceptably sized conduit for premature infants and term infants may need the diameter constrained to achieve the exact desired diameter. With prenatal diagnosis of complex congenital heart disease, the umbilical vessels could be harvested at the time of birth and preserved until the anticipated surgery. Preservation would involve whole vessel culture to ensure living, biologically active vessels with health endothelium available for implantation. This conduit may be employed in several other neonatal reconstruction applications where autologous vessels may improve outcome.

Cardiovascular reconstruction with cryopreserved umbilical veins has been described in the literature. This technique was briefly employed in peripheral vascular surgery applications. Although the umbilical veins were easy to sew and had relatively good results, they were eventually removed from marked due to ethical concerns regarding the consent of use of neonatal tissue for a non-autologous application.

Autologous umbilical vein shunts would provide an endothelialized surface and may be shaped to provide optimized hemodynamic flow conditions and improved outcomes as a shunt for neonatal cardiac surgery.

SUMMARY OF THE INVENTION

It is an object of the subject technology to provide a shunt for delivery of blood to the pulmonary circulation from the systemic circulation with improved hemodynamics including low shear stress.

In accordance with a first embodiment of the invention, the subject technology includes a shunt design that has an acute angle takeoff from the source systemic artery. The takeoff angle may be related to the difference in diameter between the shunt and the diameter of the source systemic artery distal to the shunt takeoff.

In accordance with a second embodiment of the invention, the shunt includes a fluted initial portion of the shunt is of larger diameter than the main body of the shunt. The shape of the flute may be related to the overall curvature of the shunt in the relative maximum and minimum diameters of the shunt.

In accordance with a third embodiment of the invention, a distal portion of the shunt may flare to a diameter larger than the diameter of the main body of the shunt. This flared distal aspect may be equal to the right and left or may be larger toward the right or the left.

In accordance with a fourth embodiment of the invention, a bifurcated shunt that may have equal or unequal daughter branches to direct blood flow into the right and left pulmonary arteries.

In accordance with a fifth embodiment of the invention, an umbilical cord is preserved from a child born with congenital heart disease. The umbilical cord is preserved until the umbilical vein can be dissected from the umbilical cord. The umbilical vein is then preserved until it is needed as autologous tissue for surgery for the child. The umbilical vein is prepared and implanted in the child to carry blood flow.

In accordance with a sixth embodiment of the invention, the umbilical vein may be stored in culture under flow conditions to maintain endothelial cell architecture and function.

In accordance with a seventh embodiment of the invention, the umbilical cord may be shipped to a facility after removal from the child. The umbilical cord or dissected umbilical vein may be maintained in culture for a period until the umbilical vein is needed as autologous tissue. The umbilical vein after dissected from the umbilical cord it may be shipped to the hospital where it is implanted into the child as an autologous tissue.

In accordance with an eighth embodiment of the invention, the umbilical vein may be altered in diameter or shape after it is dissected free from the umbilical cord and before it is implanted into the child. The umbilical vein may be reduced in diameter to achieve the desired blood flow after surgical implantation. The umbilical vein may be modified to achieve a particular three-dimensional shape after implanted in the child and pressurized with blood.

In accordance with a ninth embodiment of the invention, external mechanical support may be added to the umbilical vein to maintain a desired diameter and shape of the vein and prevent unwanted dilation of the vein.

It should be appreciated that the present invention can be implemented and utilized in numerous ways, including without limitation as a process, an apparatus, system, device, a kit (e.g., a kit comprising one of the platforms described herein in this first-of-use), and a method for applications now known and later developed. These and other unique features of the system disclosed herein will become more readily apparent from the following description and the accompanying drawings.

BRIEF DESCRIPTION OF THE DRAWINGS

Other aspects and many of the intended advantages of this invention will be readily appreciated, as the same becomes better understood by reference to the following detailed description, when considered in connection with the accompanying drawings wherein.

Figure 1:
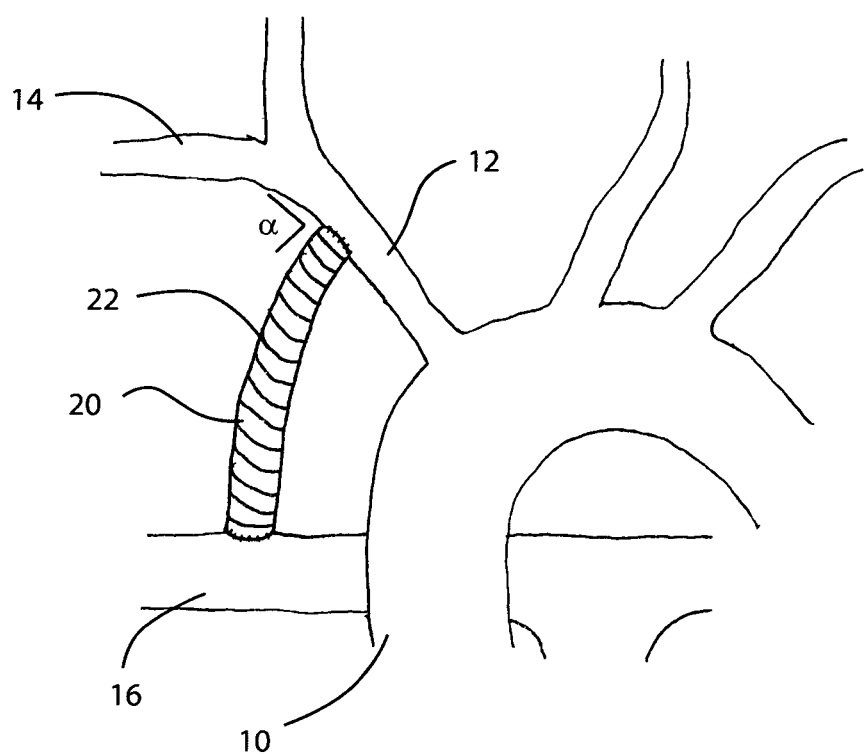
FIG. 1 illustrates an anterior view of the great vessels and a shunt positioned between the innominate artery and the right pulmonary artery.

DETAILED DESCRIPTION OF EMBODIMENTS
OF THE INVENTION

The present invention overcomes many of the prior art challenges associated with shunts for cardiac surgery. The advantages and other features of the technology disclosed herein will become more readily apparent to those having ordinarily skill in the art, and the following detailed description of certain embodiments taken into conjunction with the drawing which set forth representative embodiments of the present invention and wherein like reference numerals identify similar structural elements.

It is to be understood that the subject technology is not intended to be limited to the particular constructs and methods described in the described embodiments, as one skilled in the art can extend the concepts involved using variations which are obvious after reading the present disclosure. Although any methods and materials, similar or equivalent to those described herein, may be useful in a practice of the subject technology, certain compositions, films, methods, and materials are described below. All relative descriptions herein, such as "top," "bottom," "left," "right," "up," and "down" are with reference to the figures, and not meant to be in a limiting sense.

Referring to FIG. 1, shown is a typical shunt from a systemic artery to a pulmonary artery. This particular shunt is commonly referred to as the modified Blalock-Taussig (BT) shunt and is constructed using a polytetrafluoroethylene (PTFE) graft sewn between the innominate artery 12 which branches off the aorta 10 to the right pulmonary artery 16. The usual position would be the innominate artery 12 or R subclavian artery 14 to the right pulmonary artery 16 but many other variations of right a left source artery (including the aorta) and laterally of pulmonary artery (or main pulmonary artery) exist.

The angle α between the graft and the innominate artery (or graft and R subclavian artery) is typically around 90° but can be greater than 90°. This takeoff angle of the shunt is in sharp contrast to the normal branching angles of arteries. This sharp angulation results in flow separation within the shunt just past the anastomosis in areas of high and low shear stress within the body of the shunt. Computational fluid dynamics analysis of patients with modified BT shunts has demonstrated that these have significant perturbations of flow. In the normal arterial vasculature, there is no flow separation and there is preservation of shear stress within a narrow range throughout the entire arterial tree. Although the current modified BT shunt is straightforward to implant, resulting hemodynamics are very degraded compared to normal arteries.

Although PTFE is the commonly used shunt material, the shunt may be constructed of an alternative graft material such as but not limited to DACRON or other non-resorbable polymers, a resorbable polymer or combination of resorbable polymers, polyurethane and related materials, a preserved (homograft such as saphenous vein or umbilical vein) or fresh allograft (such as unpreserved saphenous vein, umbilical vein or arterial conduit) or autologous umbilical vein.

Figure 2:
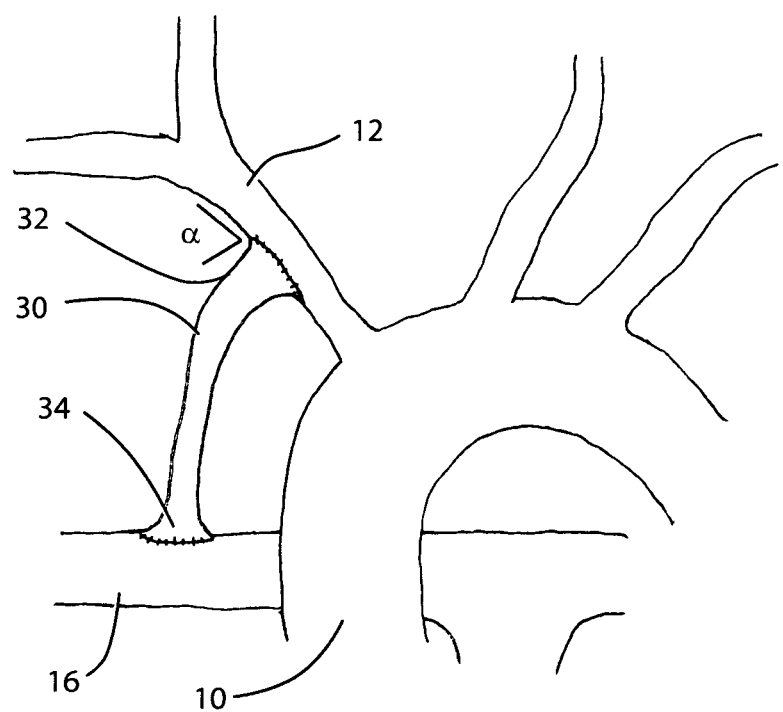
FIG. 2 illustrates an anterior view of the great vessels and a shunt positioned between the innominate artery and the right pulmonary artery with the proximal and distal aspects of the shunt fluted.

Shown in FIG. 2 is a shunt design 30 that has a fluted takeoff 32 at an angle α that may be less than 90°. The takeoff angle α may be well less than 90° and there may be a significant curvature of the shunt as it turns down to the anastomosis at the pulmonary artery. The shunt may continue to curve in such that, at the anastomosis with the pulmonary artery, shunt is angled slightly to the left to achieve balanced flow between the right and left lungs. The fluted inlet 32 may be asymmetric in the sense that the flute may be more generous towards the more proximal portion of the source artery (innominate, right subclavian, etc.) and less fluted at the distal portion of the source vessel. The body of the shunt 30 may have a diameter that is smaller than the fluted inlet 32 of the shunt. The distal aspect 34 of the shunt may also have a larger diameter than the body of the shunt and be fluted and one or both directions along the pulmonary artery. These flutes improve the flow transition into the pulmonary artery and reduce the shear forces on the posterior wall the pulmonary artery. The fluted aspect of the distal portion of the shunt 34 may be unbalanced on either side to help provide relatively balanced distribution of flow between the left and right lungs. The shape of the shunt including the proximal and distal flutes, the curvature and overall dimensions of the shunt may be optimized utilizing computational fluid dynamics. An iterative design approach may determine shape that minimizes flow disturbance and maintains the shear stress within or as near the physiologic range as possible. The idealized shape may be generalized for a range of infant weights and vessel anatomy, or it may be customized for each individual patient based on pre-operative imaging, physiologic data and other patient specific data.

There may be an adjustable external component that can alter the diameter of the shunt to provide post-operative adjustment of the shunt diameter to provide regulated blood flow through the shunt.

Figure 3:
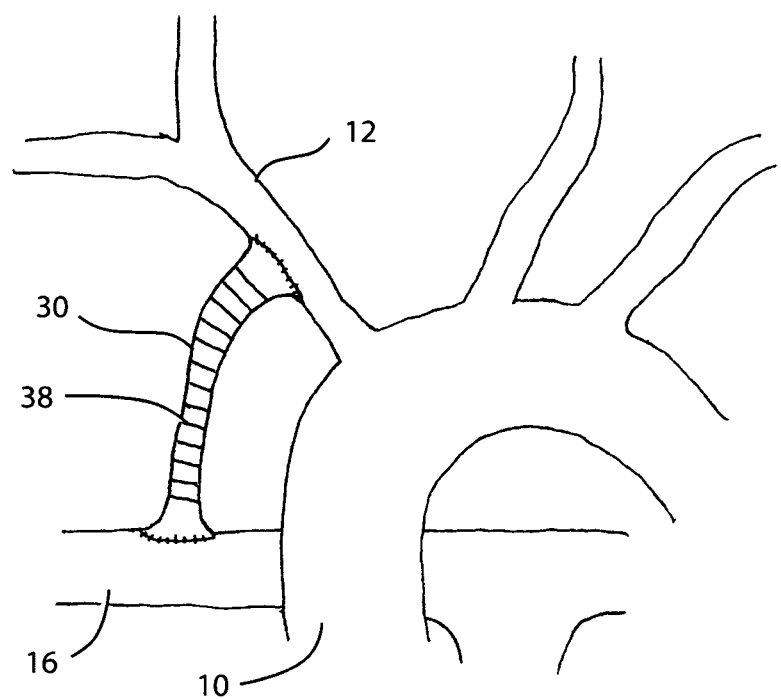
FIG. 3 illustrates an anterior view of the great vessels in a shunt positioned between the innominate artery and right pulmonary artery with a ringed support around the body of the shunt and fluted proximal and distal aspects of the shunt.

Shown in FIG. 3 is another embodiment of a hemodynamically improved shunt 30 with concentric support rings 38 that extend along at least a portion of its length to minimize the risk of kinking. The support rings 38 may be fashioned in a way to retain the desired curvature of the shunt for optimal hemodynamics.

Figure 4:
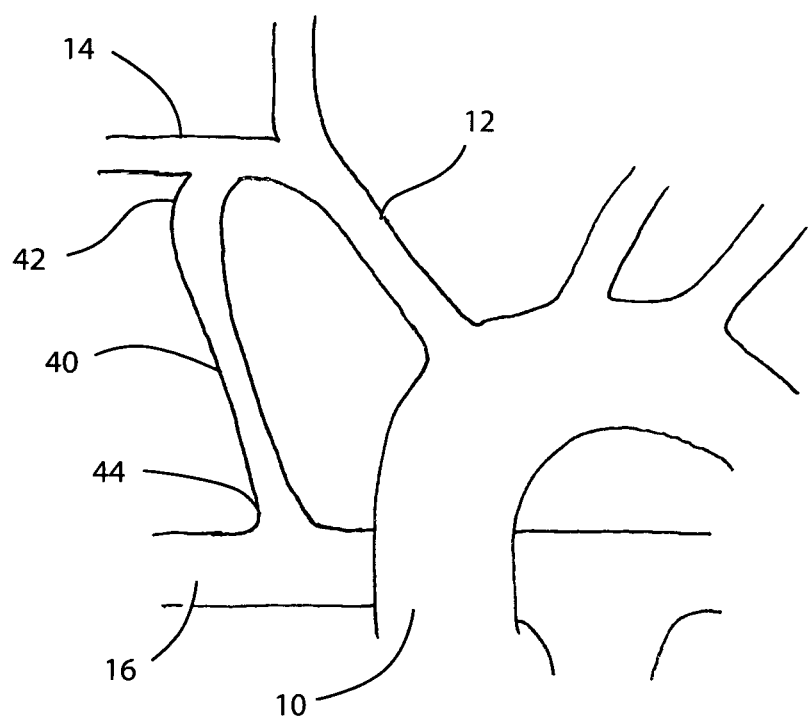
FIG. 4 illustrates an anterior view of the great vessels and a shunt positioned between the right subclavian artery and the right pulmonary artery with fluted proximal and distal aspects of the shunt.

Shown in FIG. 4 is another embodiment of a shunt 40 with a fluted proximal portion 42 and fluted distal portion 44 wherein the shunt 40 extends between the right subclavian artery 14 and the right pulmonary artery 16. Placement of the shunt off the right subclavian artery affords some additional blood flow control given the smaller size of the right subclavian artery 14 compared to the innominate artery 12.

Figure 5:
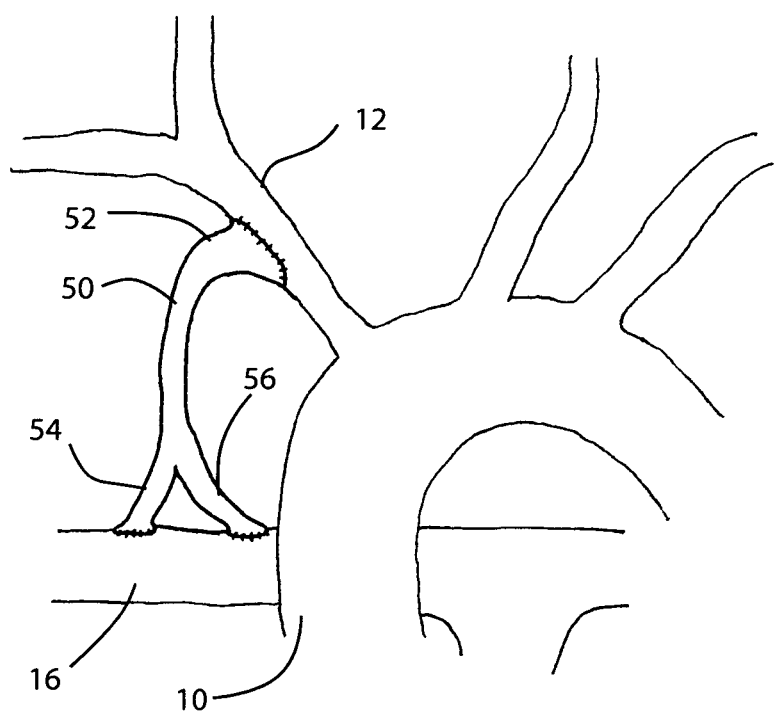
FIG. 5 illustrates an anterior view of the great vessels with a bifurcated shunt positioned between the innominate artery and the right pulmonary artery.

Shown in FIG. 5 is another embodiment of a shunt 50 extending from the innominate artery 12 to the right pulmonary artery 16 with a fluted proximal portion 52 and a bifurcation of the shunt into distal limbs 54 and 56 with limb 54 directing shunt flow to the right lung and limb 56 directing shunt flow to the left lung. The distal limbs of the shunt may be flared at their distal anastomosis to have a uniform shear stress profile as they transition to the pulmonary artery. The bifurcation may be anywhere along the shunt length such that the distal limbs may be short if the bifurcation is near the pulmonary artery or the distal limbs may be longer if the bifurcation is closer to the systemic source artery. The distal limbs may be anastomosed adjacent to each other or there may be some considerable distance even with structures between the distal limbs. For example, one distal limb and may be anastomosed to the right pulmonary artery and another distal limb anastomosed to the left pulmonary artery, on opposite sides of the aorta. The relative diameters of the distal limbs may be equal or unequal depend upon the relative size of the native pulmonary arteries and they intended flow to each lung. The sizes of the distal limbs may followed Murray's law in such that the diameter of the distal limbs ($D_{L1}$ and $D_{L2}$) are related to the diameter of the proximal portion of the shunt ($D_P$) according to the following equation:

$$D_P^3 = D_{L1}^3 + D_{L2}^3$$

Figure 6A:
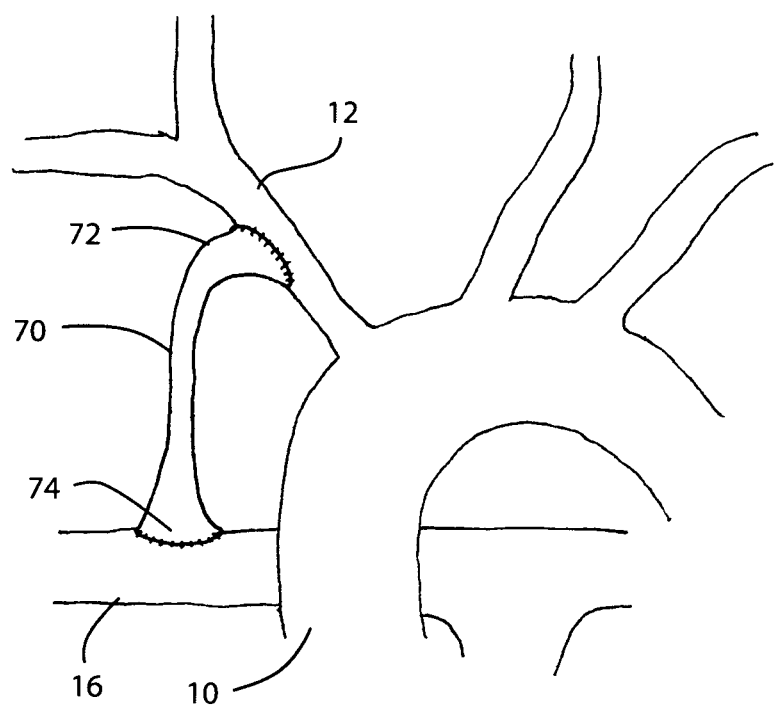
FIG. 6A illustrates an anterior view of the great vessels with a bifurcated shunt and single distal anastomosis positioned between the innominate artery and the right pulmonary artery.
Figure 6B:
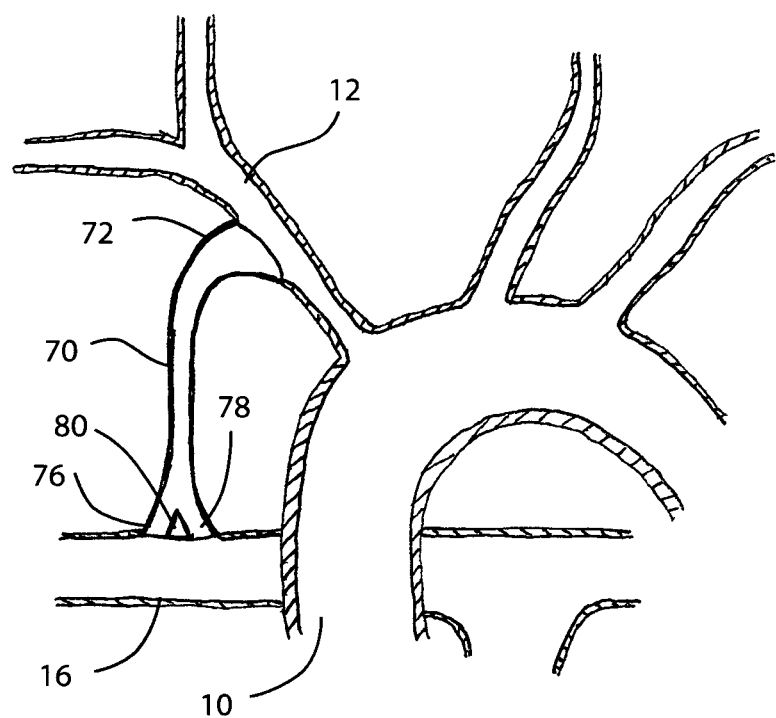
FIG. 6B illustrates a cross-sectional view of the great vessels with a bifurcated shunt and single distal anastomosis positioned between the innominate artery and right pulmonary artery.

Shown in FIG. 6A is another embodiment of a bifurcated shunt 70 that is positioned between the innominate artery 12 and the right pulmonary artery 16 with proximal fluted portion 72 of the shunt and a distal bifurcated portion 74. The distal bifurcated portion 74 of the shunt has continuous material between the two distal limbs of the bifurcation. Accordingly, the distal anastomosis is a single anastomosis comprising the two distal limbs and material between those two distal limbs. Shown in FIG. 6B, a shunt 70 extends from the innominate artery 12 to the right pulmonary artery 16 with distal limbs 76 and 78. The contiguous material 80 between the distal limbs provides both support for the shape of the distal ends and simplifies the anastomosis by enabling a single continuous anastomosis to be formed. The bifurcated shunt reduces the excess shear forces that occur on the posterior right pulmonary wall opposite the entry of a normal single lumen shunt. The direction of the blood flow toward the right and left lungs may improve the energy efficiency of the shunt and promote more uniform growth of the pulmonary arteries. Normalizing the shear stress also may minimize platelet activation and buildup of platelets and other fibrin deposits within the shunt itself. Optimization of the bifurcation of the graft will be crucial to minimize any shear stress changes in an area that may lead to platelet deposition and/or thrombus formation. In one embodiment the bifurcated shunt is constructed of PTFE, but may be created with any of the aforementioned shunt materials.

Figure 7:
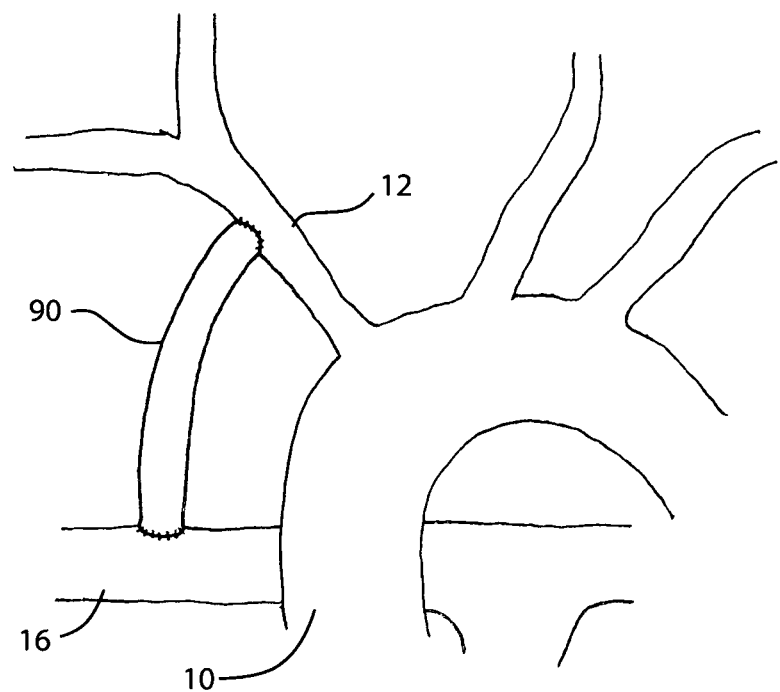
FIG. 7 illustrates an anterior view of the great vessels and a shunt positioned between the innominate artery and the right pulmonary artery.

Shown in FIG. 7 is another embodiment of a shunt 90 between the innominate artery 12 and right pulmonary artery 16. This particular shunt may be formed of a tissue including autologous umbilical vein. This autologous conduit would provide autologous endothelium within the entire shunt to minimize the chance for platelet adhesion or thrombosis. An autologous umbilical vein shunt could be positioned between the innominate artery and right pulmonary artery or the subclavian artery and right pulmonary artery or any other systemic source artery and pulmonary vascular target previously described in the literature.

Figure 8:
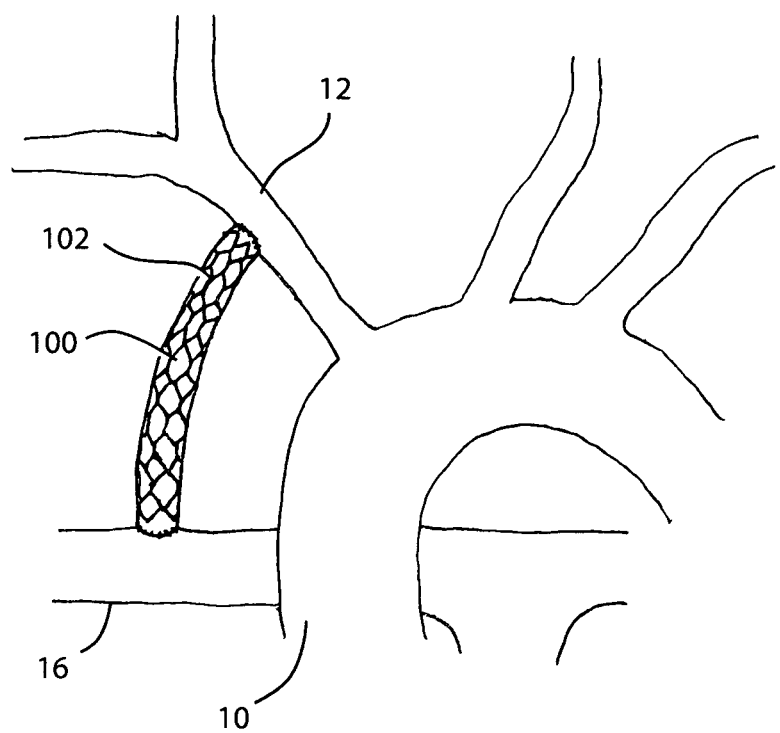
FIG. 8 illustrates an anterior view of the great vessels and an externally supported shunt positioned between the innominate artery and the right pulmonary artery.

The size of the umbilical vein is somewhat variable but generally for term infants it is significantly larger than the typical shunt. Typical diameters for umbilical veins of term infants on the order of 6 to 9 mm in diameter where the typical shunt sizes 3 to 5 mm in diameter. To provide a controlled source of pulmonary blood flow, the autologous umbilical vein shunt may need to be downsized in diameter over at least a portion of his length. There are several embodiments that may accomplish diameter control in a tissue shunt. The shunt may be narrowed along its length by a series of sutures, staples or other similar constraints. An external support may be used to constrain the diameter of the shunt as is shown in FIG. 8 where an umbilical vein shunt 100 extends from the innominate artery 12 to the right pulmonary artery 16 with an external support 102. Such supports include a stent or stent-like support including ringed support, mesh or mesh-like support. The umbilical vein may be secured to the external support in one or more locations with suture or other means including, but not limited to, adhesives. Other alternatives include a perforated vascular graft. One particular embodiment may include supporting the umbilical vein with the eSVS NITINOL mesh that has been developed by Kips Bay Medical (Minneapolis, Minn.). The stent or other external support may extend over a portion of the umbilical vein or the entire length of the umbilical vein.

Optimization of the shape of the autologous umbilical vein to normalize the shear stress within the shunt into normal or near normal physiologic range may be important to preserve the health of the endothelium of the shunt and minimize the risk of platelet deposition and thrombosis. As the umbilical veins are of a generous diameter compared to the intended diameter of the shunt, umbilical veins may be shaped to include flared proximal and distal portions as described above and detailed in FIGS. 2, 3 and 4. The external support in the form of the stent or other support as described may be used to both constrain the diameter of the vein to prevent further expansion as well as maintain the optimized shape of the vein. The shape of the stent or other support may be configured to fit the exact anatomy of the child and optimize the flow within the umbilical vein shunt. This may include changing the shape of the stent or other external support like material at the time of the implantation operation of the umbilical vein shunt.

Use of the stent or stent-like support to provide narrowing of the shunt to the desired diameter (as the only source of narrowing or in addition to mechanical narrowing of the shunt with suture material for example) may provide a means of enlarging the shunt with balloon dilation in a procedure after implantation of the shunt. This may be useful in children that have inadequate pulmonary blood flow in the near term after the operation, or alternatively in children who need additional pulmonary blood flow even months after the initial operation.

Procurement of the umbilical veins from children with congenital heart disease just after birth would need to occur in sterile fashion after vaginal or C-section delivery. The umbilical vein would need to be placed in a preserving solution such as UW solution with antibiotics. The umbilical vein would need to be stored in culture for several days or weeks until the child was taken to surgery. Storage options for the vein would include cold culture at 4° C. in media with antibiotics in static conditions or in a bioreactor or other system that could deliver flow to the umbilical vein. Alternatively, the umbilical vein could be stored statically or under flow conditions in culture at 37° C. Media options include standard culture media with animal or human serum including potentially autologous serum. Human plasma lysate may be used as a serum replacement to avoid the use of animal products. UW solution with human plasma lysate may be another culture media option. The umbilical vein would need to be dissected free from the umbilical cord either prior to or after the period of culture.

The dissection and culture of the umbilical vein may occur at the site of delivery, within the facility where the child's surgery will occur or may be done in a separate location. This may include harvest of the umbilical cord at the time of delivery and then shipping the umbilical cord to a separate location where the cord can be dissected in the umbilical vein stored in culture. At the time the child surgery is scheduled the umbilical vein could be shipped to the hospital where the surgery would occur in time for implantation. Another alternative may be to store the entire umbilical cord in culture and then dissected the umbilical vein out at the time of implantation surgery.

In another embodiment, and allogenic umbilical vein may be used either fresh or after cryopreservation as a shunt in a newborn or child. If the allogenic umbilical vein were to be used without preservation, a degree of immunosuppression would be required in the recipient child.

In another embodiment, a hemodynamically optimized PTFE shunt may be used in the right ventricle to pulmonary artery (RV to PA) conduit position. Currently 4 to 6 mm PTFE grafts are currently used in neonatal surgery as RV to PA conduits, with one example being a Stage I reconstruction for hypoplastic left heart syndrome. The proximal anastomosis of this RV to PA conduit is typically done by inserting the proximal end of the ringed PTFE graft through the heart muscle and slightly into the right ventricular cavity. The distal end is anastomosed to the pulmonary artery to the left or right of the aorta. It would be beneficial to improve hemodynamics and improve the balance of flow between the left and right lungs to have a slightly flared portion of the distal aspect of this graft. Like the systemic to pulmonary artery shunts, the distal aspect of the RV to PA conduit graft may be flared symmetrically, or maybe asymmetrically flared to intentionally balanced flow between the left and right lungs.

In another embodiment, the RV to PA conduit may be bifurcated as described above in FIGS. 5, 6A and 6B. The distal limbs the bifurcated graft may be anastomosed on the same side or opposite sides of the aorta.

To minimize the stenosis and reintervention rate of RV to PA conduits, an endothelialized conduit may be the ideal option. An autologous umbilical vein may be used as a RV to PA conduit for neonatal surgery. In this embodiment, the umbilical vein may be anastomosed directly to the myocardium proximally and to the pulmonary arteries distally. In another embodiment, a composite RV to PA conduit may be used with a proximal portion being a ringed PTFE graft and the distal portion being an autologous umbilical vein segment.

There may be clinical value in having a valved RV to PA conduit for neonatal surgery such as the Stage I reconstruction. In another embodiment, an RV to PA conduit (either a composite conduit with a PTFE portion or a vein only conduit) may have a bicuspid or tricuspid valve created within the conduit utilizing autologous umbilical vein or autologous amnion as the leaflet materials. These materials may be sewn into the conduit using fine sutures such as 7-0 or 8-0 prolene or may be adhered to the interior of the umbilical vein using laser bonding with Rose Bengal as has been described. These autologous valves within the autologous umbilical vein may provide adequate valvular function until the subsequent operation in these children.

INCORPORATION BY REFERENCE

All patents, published patent applications and other references disclosed herein are hereby expressly incorporated in their entirety by reference. It should be understood that the forgoing disclosure and description of the present invention are illustrated and explanatory thereof and various changes in the size, shape, and material composition, as well as in the description of the embodiments, may be made without departure from the spirit of the invention as defined by the appended claims.

What is claimed is:

1. An umbilical vein for use as a shunt between a systemic artery and pulmonary artery wherein said umbilical vein is autologous, and further comprises proximal and distal portions that are larger in diameter than the central portion to achieve minimal fluid separation into and out of the graft, wherein said central portion is narrowed along at least a portion of its length to provide a controlled amount of blood flow to the lungs.

2. The umbilical vein according to claim 1, wherein external support aver at least a portion of the shunt provides narrowing of the shunt to limit blood flow.

3. The umbilical vein according to claim 2, wherein an external support controls the diameter of the vein and maintains a hemodynamically optimized shape.

4. An autologous umbilical vein for use as a shunt between a ventricular chamber of the heart and a pulmonary artery wherein said autologous umbilical vein is narrowed along at least a portion of its length to provide a controlled amount of blood flow to the lungs.

5. The autologous umbilical vein according to claim 4, wherein there is a functional valve created within the shunt utilizing amnion or autologous umbilical vein tissue.

6. The autologous umbilical vein according to claim 4, wherein a portion of the shunt is a non-resorbable vascular graft and a portion of the shunt is an umbilical vein.

\* \* \* \* \*